(12) United States Patent
Minor (10) Patent No.: US 9,465,910 B2
(45) Date of Patent: Oct. 11, 2016

(54) DIAGNOSTIC METHODS AND DEVICES FOR MONITORING CHRONIC GLYCEMIA

(71) Applicant: James M. Minor, Newark, DE (US)

(72) Inventor: James M. Minor, Newark, DE (US)

(73) Assignees: James Minor, Newark, DE (US); Alan Cannon, Lakeport, CA (US)

( * ) Notice: Subject to any disclaimer, the term of this patent is extended or adjusted under 35 U.S.C. 154(b) by 698 days.

(21) Appl. No.: 13/895,054

(22) Filed: May 15, 2013

(65) Prior Publication Data

US 2013/0311102 A1 Nov. 21, 2013

Related U.S. Application Data

(60) Provisional application No. 61/647,165, filed on May 15, 2012.

(51) Int. Cl.
  *G01N 33/48* (2006.01)
  *G06F 19/10* (2011.01)
  *G06F 19/00* (2011.01)

(52) U.S. Cl.
  CPC ............. *G06F 19/10* (2013.01); *G06F 19/345* (2013.01); *G06F 19/3431* (2013.01)

(58) Field of Classification Search
  CPC ...................................................... G06F 19/10
  USPC ........................................................ 702/19
  See application file for complete search history.

(56) References Cited

U.S. PATENT DOCUMENTS

| | | |
|---|---|---|
| 5,009,230 A | 4/1991 | Hutchinson |
| 5,141,868 A | 8/1992 | Shanks et al. |
| 5,286,362 A | 2/1994 | Hoenes et al. |
| 5,437,999 A | 8/1995 | Diebold et al. |
| 5,708,247 A | 1/1998 | McAleer et al. |
| 5,951,836 A | 9/1999 | McAleer et al. |
| D428,150 S | 7/2000 | Ruf et al. |
| 6,241,862 B1 | 6/2001 | McAleer et al. |
| 6,285,125 B1 | 9/2001 | Mizuno |
| 6,413,410 B1 | 7/2002 | Hodges et al. |
| 6,579,690 B1 | 6/2003 | Bonnecaze et al. |
| 6,733,655 B1 | 5/2004 | Davies et al. |
| 8,372,261 B2 | 2/2013 | Feldman et al. |
| 8,409,093 B2 | 4/2013 | Bugler |
| 8,425,416 B2 | 4/2013 | Brister et al. |
| 2002/0058906 A1 | 5/2002 | Lebel et al. |
| 2007/0232872 A1 | 10/2007 | Prough et al. |
| 2009/0018406 A1 | 1/2009 | Yodfat et al. |
| 2009/0030398 A1 | 1/2009 | Yodfat et al. |
| 2009/0048152 A1 | 2/2009 | Yodfat et al. |
| 2010/0330594 A1 | 12/2010 | Hart et al. |
| 2011/0119081 A1 | 5/2011 | Vespasiani |
| 2011/0230744 A1 | 9/2011 | Ribas Ripoll et al. |
| 2011/0264378 A1 | 10/2011 | Breton et al. |
| 2011/0319322 A1 | 12/2011 | Bashan et al. |
| 2012/0245556 A1 | 9/2012 | Kovatchev et al. |
| 2012/0246102 A1 | 9/2012 | Sudharsan |
| 2012/0330119 A1 | 12/2012 | Shaanan et al. |
| 2013/0030358 A1 | 1/2013 | Yodfat et al. |
| 2013/0035865 A1 | 2/2013 | Mayou et al. |
| 2013/0035871 A1 | 2/2013 | Mayou et al. |
| 2013/0041343 A1 | 2/2013 | Toumazou et al. |
| 2013/0085349 A1 | 4/2013 | Shaanan et al. |
| 2013/0085358 A1 | 4/2013 | Crouther et al. |
| 2013/0098775 A1 | 4/2013 | Pei et al. |
| 2013/0102018 A1 | 4/2013 | Schentag et al. |
| 2013/0102867 A1 | 4/2013 | Desborough et al. |
| 2013/0103424 A1 | 4/2013 | Brown |
| 2013/0108598 A1 | 5/2013 | Oresic et al. |

OTHER PUBLICATIONS

Holt, TA, Editor, "Complexity for Clinicians", Radcliffe, 2004, pp. 78-79.
Matrex and International Diabetes Center, Staged diabetes management: a systematic approach, John Wiley & Sons, 2006, p. 13.
The Art and Science of Diabetes Self-Management Education, American Association of Diabetes Educators, 2006, pp. 145, 218.
Martinet-Peignouz et al., "Accurate model predicting sustained response at week 4 of therapy with pegylated interferon with ribavirin in patients with chronic hepatitis C", Journal of viral Hepatitis, 13(10): 701-707, 2006.
Minor, "Similarity Least Square (SLS) method for Functional Clustering by Using Stimulus Features to Model and Predict response", slsguy.com, 2004.
Rickey et al., "Predictors of Improvement in lower Urinary Tract Symptoms after Sacrolpopexy", Society for Urodynamics and Female Urology, Phoenix, AX (oral presentation), Feb. 2011.
Devaney, "An introduction to chaotic dynamical systems", Addison-Weley Publishing Co., 1989, pp. 4-5.
Parker, "Practical numerical algorithms for chaotic systems", Springer-Verlag, 1989, pp. 4-5.
Cohen et al., "Red cell life span heterogenicity in hematologically normal people is sufficient to alter HbA1c", Blood, Nov. 15, 2008, Abstract.
Kahn et al., "Translating the A1C Assay", Diabetes Care, vol. 31, No. 8, Aug. 2008, pp. 1704-1707.
Kroll, "Biological variation of glucose and insulin includes a deterministic chaotic component", Biosystems 50 (1999) pp. 189-201.
Nathan et al., "Translating the A1c Assay into Estimated Average Glucose Values", Diabetes Care, 31:1473-1478, 2008.
Wilson et al., "Persistence of Individual Variations in Glycated Hemoglobin", Diabates Care, vol. 34, Jun. 2011, pp. 1315-1317.

*Primary Examiner* — Jerry Lin
(74) *Attorney, Agent, or Firm* — Alan W. Cannon (57) ABSTRACT

Computer apparatus, non-transitory computer readable media and methods for receiving daily vectors of measured blood glucose level values ordered by daily-defined time points over multiple days distributed over a predefined time period; calculating a vector average; calculating a chronic glycemia value based on the vector average modified by a universal term based on the centroid of an attractor basin; receiving subsequent daily vectors of blood glucose level values measured at subsequent defined time points after the predefined time period; calculating an updated vector average; calculating a subsequent chronic glycemia value based on the updated vector average modified by the universal term based on the centroid of the attractor basin estimated from the orbit; and outputting the chronic glycemia value and subsequent chronic glycemia value.

23 Claims, 5 Drawing Sheets

Distribution of Offsets versus Insulin

Fig. 7

DIAGNOSTIC METHODS AND DEVICES FOR MONITORING CHRONIC GLYCEMIA

CROSS-REFERENCE

This application claims the benefit of U.S. Provisional Application No. 61/647,165, filed May 15, 2012, which application is hereby incorporated herein, in its entirety, by reference thereto.

FIELD OF THE INVENTION

This invention relates generally to the field of diagnostic processes and devices for monitoring and identifying critical clinical parameters in diseases requiring comprehensive vigilant attention such as CVD, asthma, psychosis, addiction, diabetes, transplants. Moreover it pertains specifically to such process to produce a useful new diagnostic for chronic glycemia utilizing data collected by a medical device, and a device for collecting, that measures blood glucose levels of diabetes patients and stores date representing blood glucose levels electronically in the device and/or in a remote system.

BACKGROUND OF THE INVENTION

The A1C assay, expressed as the percent of hemoglobin that is glycated, measure chronic glycemia and is widely used to judge the adequacy of diabetes treatment an adjust therapy. Day-to-day management is guided by self-monitoring of capillary glucose concentrations(milligrams per deciliter or millimoles per liter), e.g., see Nathan et al., "Translating the A1C Assay Into Estimated Average Glucose Values" Diabetes Care, Vol. 31, No. 8, August, 2008, which is hereby incorporated herein, in its entirety, by reference thereto. Chronic glycemia, commonly characterized by average glucose levels in a patient and therefore denoted AG, is the persistent mean level of blood glucose (BG) over a threshold value and over an extended period of multiple days and is related to diabetes progression and complications. The threshold level may vary among different treatment regimens, but is generally a glucose level higher than 11.1 mmol/l (200 mg/dl). Reference ranges for blood tests are 11.1 mmol/l, but symptoms may not start to become noticeable until even higher values such as 250-300 mg/dl or 15-20 mmol/l. A subject with a consistent range between 100 and 126 (American Diabetes Association guidelines) is considered hyperglycemic, while above 126 mg/dl or 7 mmol/l is generally held to have diabetes. Chronic levels exceeding 7 mmol/l (125 mg/dl) can produce organ damage. Controlling chronic glycemia is a key factor in the clinical management of diabetes healthcare as described in established medical reference books, e.g., see International Diabetes Center, *Staged Diabetes Management*, John Wiley & Sons, 2006, p. 13 and *The Art and Science of Diabetes Self-Management Education*, American Association of Diabetes Educators, 2006, pp 145, 218, both of which are hereby incorporated herein, in their entireties, by reference thereto.

The fraction or percent of glycated hemoglobin, denoted HbA1C or A1C, is currently used to infer the level of AG with a standard error ranging from ±10 to ±25 mg/dL, e.g., see Nathan et al., "Translating the A1C Assay Into Estimated Average Glucose Values" Diabetes Care, Vol. 31, No. 8, August, 2008, and Kahn et al., "Translating the A1C Assay", diabetes Care, Vol. 31, No. 8, August, 2008, both of which are hereby incorporated herein, in their entireties, by reference thereto.

However, as described in recent publications, the significant impact of personal factors on the association of A1C with chronic glycemia compromises this inference, e.g., see Cohen et al., "Red cell life span heterogenicity in hematologically normal people is sufficient to alter HbA1c", Blood, 15 Nov. 2008, Vol. 112, No. 10, PP 4284-4291 and Wilson et al., "Persistence of Individual Variations in Glycated Hemoglobin", Diabetes Care, Vol. 34, June 2011, pp 1315-1317, both of which are hereby incorporated herein, in their entireties, by reference thereto. Despite newer methods that correct for some personal factors A1C is still an inherently slow measure of chronic glycemia requiring typically 3 months to fully equilibrate and hence is insensitive to immediate important trends.

There is a need for timelier diagnostics to directly track chronic glycemia with better precision based on casual patient data, typically collected at self-monitoring-blood-glucose (SMBG) events.

There is a need for timelier diagnostics that can capture and be used to identify long-term (gradient) trends in the diabetic status specific to each patient.

It would further be desirable to provide timelier diagnostic capabilities as incorporated into a device to perform the diagnostic or in devices such as blood glucose monitoring devices currently used by patients and doctors.

SUMMARY OF THE INVENTION

According to one aspect of the present invention, a computer apparatus is provided that includes at least one processor; and programming which, when executed by the at least one processor, performs a process including: receiving daily vectors of measured blood glucose level values ordered by daily-defined time points over multiple days distributed over a predefined time period; calculating a vector average from the daily vectors; calculating a chronic glycemia value based on the vector average modified by a universal term based on the centroid of an attractor basin estimated by an orbit established by the daily vectors calculated from the blood glucose levels measured at the defined time points over multiple days distributed over the predefined time period; receiving subsequent daily vectors of blood glucose level values measured at subsequent defined time points after the predefined time period; calculating an updated vector average from the daily vectors and subsequent daily vectors; calculating a subsequent chronic glycemia value based on the updated vector average modified by the universal term based on the centroid of the attractor basin estimated from the orbit; and outputting the chronic glycemia value and subsequent chronic glycemia value to show a trend over time of chronic glycemia status.

In at least one embodiment, the programming, when executed by said at least one processor, outputs the chronic glycemia value after the calculating a chronic glycemia value.

In at least one embodiment, calculating the chronic glycemia value comprises using the formula: $AG_S = \text{offset}_S + \text{vector a} * \text{vector BG mean} \pm \text{expected error}$; where "$AG_S$" refers to the chronic glycemia value, * indicates a vector dot product operation, $\text{offset}_S$ is a patient-specific constant, "vector a" is a vector that refers to the universal term," vector BG mean" is a vector that refers to the vector average, "S"

indexes each subject, and the expected error results from both statistical uncertainty and dynamic uncertainty of chaos theory.

In at least one embodiment, the vector "a" is a two-dimensional vector comprising components "a[1]" and "a[2]", and wherein $0<a[1]<0.5$ and $0<a[2]<0.5$.

In at least one embodiment, the vector "a" is a two-dimensional vector comprising components "a[1]" and "a[2]", and wherein $0<a[1]<1.0$ and $0<a[2]<1.0$.

In at least one embodiment, $a[1]=a[2]=0.475$, and expected error=$\pm 2.910$ mg/dL.

In at least one embodiment, the expected error is less than $\pm 10$ mg/dL (glucose/blood).

In at least one embodiment, the expected error is about $\pm 2.91$ mg/dL (glucose/blood).

In at least one embodiment, calculating a chronic glycemia value comprises calculating a relative chronic glycemia value using the formula: $AG_S$=vector a*vector BG mean$\pm$expected error; where "$AG_S$" refers to the chronic glycemia value, * is a vector dot product, "vector a" is a vector that refers to the universal term, "vector BG mean" is a vector that refers to the vector average, "S" indexes each subject, and the expected error results from both statistical uncertainty and dynamic uncertainty of chaos theory.

In at least one embodiment, the apparatus is incorporated in a personal blood glucose monitor.

In at least one embodiment, the programming, when executed by the at least one processor, calculates at least one scatter value based on a diameter of the orbit, and outputs the at least one scatter value, wherein each the at least one scatter value is calculated by averaging diameter values of the orbit over multiple adjacent time periods.

In another aspect of the present invention, a medical apparatus is provided that includes a blood glucose monitoring device configured to take and output blood glucose measurements, including at least one processor; the apparatus further comprising programming which, when executed by the at least one processor, performs a process including: receiving daily blood glucose level values measured by the blood glucose monitoring device at daily-defined time points over multiple days distributed over a predefined time period; calculating a daily vector of the measured blood glucose level values received for each day, respectively; calculating a vector average from the daily vectors having been calculated; calculating a chronic glycemia value based on the vector average modified by a universal term based on a centroid of an attractor basin defined by a vector orbit established by the blood glucose levels measured at the defined time points over multiple days distributed over the predefined time period; receiving subsequent blood glucose level values measured by the blood glucose monitoring device on one or more days after the predefined time period; calculating a subsequent daily vector of measured additional blood glucose level values received for each day, respectively, after the predefined time period; calculating an updated vector average from the daily vectors and subsequent daily vectors; calculating a subsequent chronic glycemia value based on the updated vector average modified by the universal term based on the centroid of the attractor basin estimated from the vector orbit; and outputting the chronic glycemia value and subsequent chronic glycemia value to show a trend over time of chronic glycemia status.

In another aspect of the present invention, a non-transitory computer readable medium is provided that includes one or more sequences of instructions for performing chronic glycemia trending, wherein execution of the one or more sequences of instructions by one or more processors causes the one or more processors to perform a process comprising: receiving a daily vector of measured blood glucose level values ordered by daily defined time points over multiple days distributed over a predefined time period; calculating a vector average from the daily vectors of blood glucose levels received; calculating a chronic glycemia value based on the vector average modified by a universal term based on a centroid of an attractor basin estimated by an orbit established by the daily vectors of the blood glucose levels measured at the defined time points over multiple days distributed over the predefined time period; receiving at least one additional daily vector of blood glucose level values measured at additional defined time points after the predefined time period; calculating an updated average vector blood glucose level from the daily vectors and the at least one additional daily vector; calculating a subsequent chronic glycemia value based on the updated vector average modified by the universal term based on the centroid of the attractor basin estimated from the orbit; and outputting the chronic glycemia value and subsequent chronic glycemia value to show a trend over time of chronic glycemia status.

In at least one embodiment, the non-transitory computer readable medium further includes instructions which, when executed by the one or more processors, cause the one or more processors to output the chronic glycemia value after the calculating a chronic glycemia value.

In at least one embodiment, calculating a chronic glycemia value comprises calculating the chronic glycemia value using the formula: $AG_S$=offset$_S$+a*BG mean$\pm$expected error; where "$AG_S$" refers to the chronic glycemia value, * indicates a vector dot product operation, offset, is a patient-specific constant "a" is a vector that refers to the universal term, "BG mean" is a vector that refers to the vector average, "S" indexes each subject, and the expected error results from both statistical uncertainty and dynamic uncertainty of chaos theory.

In at least one embodiment, the vector "a" is a two-dimensional vector comprising components "a[1]" and "a[2]", and wherein $0<a[1]<0.5$ and $0<a[2]<0.5$.

In at least one embodiment, the expected error is less than $\pm 8$ mg/dL (glucose/blood).

In at least one embodiment, the expected error is about $\pm 2.910$ mg/dL (glucose/blood).

In at least one embodiment, the non-transitory computer readable medium further includes instructions which, when executed by the one or more processors, cause the one or more processors to calculate at least one scatter value based on a diameter variation of the orbit over time, and output the at least one scatter value.

In another aspect of the present invention, a method for tracking chronic glycemia is provided that includes: receiving a daily vector of measured blood glucose level values ordered by daily defined time points over multiple days distributed over a predefined time period; calculating a vector average from the blood glucose levels received over multiple days; calculating a chronic glycemia value based on the vector average modified by a universal term based on a centroid of an attractor basin estimated by an orbit established by the vectors of the blood glucose levels measured at the defined time points over multiple days distributed over the predefined time period; receiving at least one additional daily vector of blood glucose level values measured at additional defined time points after the predefined time period; calculating an updated vector average from the blood glucose levels and the additional blood glucose levels received; calculating a subsequent chronic glycemia value based on the updated vector average modified by the universal term based on the centroid of the attractor basin estimated by the orbit; and outputting the chronic glycemia value and subsequent chronic glycemia value to show a trend over time of chronic glycemia status.

In at least one embodiment, calculating a chronic glycemia value comprises calculating the chronic glycemia value using the formula: $AG_S = \text{offset}_S + \text{vector a} * \text{vector BG mean} \pm \text{expected error}$; where "$AG_S$" refers to the chronic glycemia value, * indicates a vector dot product operation, $\text{offset}_S$ is a patient-specific constant, "vector a" is a vector that refers to the universal term, "vector BG mean" is a vector that refers to the vector average, "S" indexes each subject, and the expected error results from both statistical uncertainty and dynamic uncertainty of chaos theory.

In at least one embodiment, the expected error is less than ±10 mg/dL (glucose/blood).

In at least one embodiment, the method includes calculating at least one scatter value based on a diameter change of the orbit.

These and other features of the invention will become apparent to those persons skilled in the art upon reading the details of the apparatus, devices, non-transitory computer readable media and methods as more fully described below.

DETAILED DESCRIPTION OF THE INVENTION

Before the present apparatus, devices, methods and non-transitory computer readable media are described, it is to be understood that this invention is not limited to particular embodiments or disease described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a blood glucose measurement or reading" includes a plurality of such blood glucose measurements or readings and reference to "the orbit" includes reference to one or more orbits and equivalents thereof known to those skilled in the art, and so forth.

The publications discussed herein are provided solely for their disclosure prior to the filing date of the present application, and each is incorporated herein, in its entirety, by reference thereto. Nothing herein is to be construed as an admission that the present invention is not entitled to antedate such publication by virtue of prior invention. Further, the dates of publication provided may be different from the actual publication dates which may need to be independently confirmed.

Definitions

A "patient-specific constant", as used herein, refers to a constant value in an equation that applies particularly to the patient that is being addressed by application of the equation.

A "universal term", as used herein, refers to a functional JMM term, whose with functional form and clinical evaluation that applies to all patients. For example, the term "a" used in equations herein and its vector dot-product form applied to a vector of each patient's clinical measurements is a universal functional term.

An "orbit", as used herein, refers to the path/locus tracked in phase space by a vector of dynamic variables over time.

An "attractor centroid" as used herein, refers to the region in phase space that is the ultimate destination of a dynamic process. The orbit tends to be trapped or localized within the attractor basin like the earth's moon.

DETAILED DESCRIPTION

In view of the limitations now present in the prior art, the present invention provides new and useful diagnostics for chronic glycemia (AG) which are simpler, more universally usable and more versatile than known diabetes diagnostics of this type. In at least one embodiment, the present invention provides a new diagnostic for chronic glycemia, developed using nonlinear dynamics and deterministic chaos theory, that can track chronic glycemia on a daily basis using typical daily blood glucose readings. In at least one embodiment, the present invention applies state space concepts to the inter-day variations of AG, using daily BG readings to monitor AG trends. In at least one embodiment, the present invention can track chronic glycemia on a daily basis using one or two specific daily blood glucose readings. The present invention can improve healthcare of diabetes patients and reduce risk of costly serious complications. Conveniently, in at least one embodiment the apparatus of the present invention can be used by and/or incorporated in medical devices that measure and monitor blood glucose. Thus, any or all of the diagnostics described herein can be incorporated into any existing device configured to take blood glucose readings, including, but not limited to blood glucose monitors manufactured and marketed for personal use. Additionally, any or all of the diagnostic described herein can be processed by multiple computing devices, over a network, including, but not limited to the Internet, with communication of data being performed either wirelessly or by wired connection. As one non-limiting example, a patient's blood glucose monitor can wirelessly transmit blood glucose readings taken by the patient, which can be received an processed according to algorithms and methods described herein, by a medical internet service, or at a hospital or doctor's office. Additionally, or alternatively, blood glucose readings and/or diagnostic results produced from the present invention can be transferred and stored in a remote location. In at least one embodiment of the present invention, a diagnostic is provided that can be used to evaluate the degree of BG fluctuations (scatter) for risk assessment of glycemia, and unusual and/or critical levels of BG.

In at least one embodiment, the present invention includes an apparatus for monitoring and/or tracking chronic glycemia from the inter-day nonlinear dynamics of diabetes and its patient interactions. Daily measurements of blood glucose (BG) levels are made at defined time points over multiple days distributed over a specified time span to track chronic glycemia on a daily basis with unprecedented precision. For best results, the measurements are taken on all days of the week (Monday, Tuesday, Wednesday, Thursday, Friday, Saturday and Sunday) to provide the most complete orbit from which to process calculations as described in more detail below. However, any subset that defines the orbit is adequate. The defined time points generally coincide with the standard events of the self-monitoring-blood-glucose (SMBG) protocol.

Specifically, for all patients the apparatus calculates a universal term from daily BG levels from multiple days distributed over a specified span of time. According to the state-space phase portraits derived from the inter-day nonlinear dynamics of the daily BG levels, after one complete phase orbit (typically, but not necessarily generated from BG levels measured on each of Monday Tuesday, Wednesday, Thursday, Friday, Saturday and Sunday, although the days need not be successive, as they could be, for example, from days over a two-week time span) this universal term tracks serial AG trending on a daily basis with a better precision than known heretofore. The precision is less than about ±10 mg glucose per deciliter of blood (mg/dL) or less than about ±8 mg/dL, less than about ±6 mg/dL, less than about ±5 mg/dL, less than about ±4 mg/dL, or less than about ±3 mg/dL, preferably the precision is less than about ±3 mg/dL, typically about ±2.910 mg/dL. As noted above, a complete orbit typically requires seven different week days over one or two adjacent weeks. The process also defines a patient-specific constant that converts the relative tracking values to absolute AG units. The constant measures an important property of diabetes which is the persistence of daily blood glucose excursions from ambient levels caused by meals/snacks, unusual activity (exercise), or effective medications, i.e., insulin injections.

In at least one embodiment, the diagnostic can be carried out by incorporating it into a device configured to take blood samples of a patient. In addition to the software incorporated into the device need to calculate the current blood sugar value, the present diagnostic is also programmed into the device, the processor and clock of which are employed to carry out the diagnostic, calculate values as descried both above and below, and calculate AG. These values can be stored in the device and/or transmitted to another device for further processing, data compilation, etc. and./or printed out. In reference to such, there is to be a clear understanding that the present invention is not limited to the method or detail of construction, fabrication, material, or application of use described and illustrated herein. Any other variation of fabrication, use, or application should be considered apparent as an alternative embodiment of the present invention.

Figure 1:
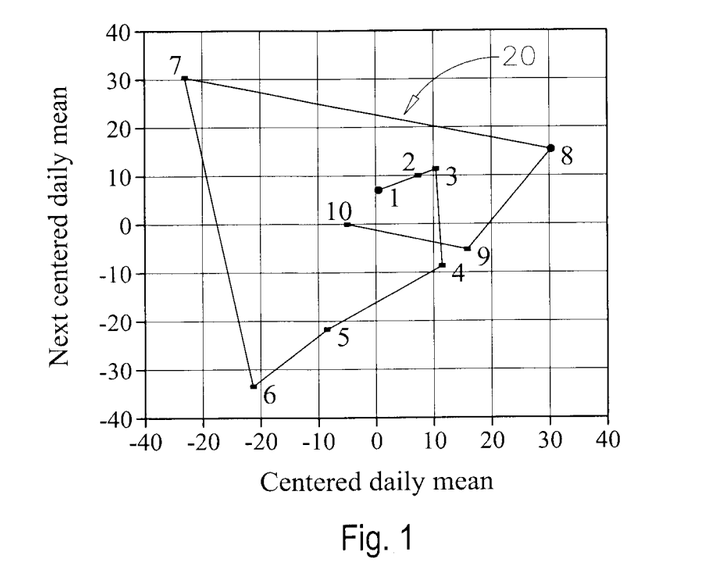
FIG. 1 is a graph plotting inter-day attractor orbit properties of average daily blood glucose levels measured from a patient, according to an embodiment of the present invention.

Referring now to the drawings, FIG. 1 is a graph plotting inter-day attractor orbit properties if average daily blood glucose levels measured from a patient, wherein a vector of two strategic blood glucose level measurements were made for each of days 1-11 (one measurement in the morning before breakfast, and one measurement before bedtime) FIG. 1 illustrates the nonlinear dynamic basis for calculations performed in the present invention for tracking chronic glycemia, as well as for calculating scatter. Both axes are centered at "0" on the attractor centroid of the daily mean in units of mg glucose per deciliter of blood (mg/dL). The vector of dynamic variables rotates about a location in phase space which is the centroid of an attractor basin/region. This region can drift over time due to the impact of external factors (factors not within the dynamic system). Time intervals of slow drift can estimate its centroid by averaging adjacent estimates of AG. Plotting the vector orbit relative to its centroid clarifies the pattern. The horizontal axis plots the daily mean (average) values of the blood glucose measurements, relative to the attractor centroid value (designated zero), and the vertical axis plots the next centered daily mean (average values of the blood glucose measurements, relative to the attractor centroid value (also designated zero). The indices 1-10 indicated monitored days in chronological order as distributed over a fixed interval of time (in this case, two weeks). For example, reference numeral "1" shows the mean BG for day 1 plotted against the mean BG for day 2, and reference numeral "10" shows the mean BG for day 10 plotted against the mean BG for day 11, etc. This is a valuable but simple established method to identify deterministic chaos dynamics from one channel of data.

The orbit 20 and its properties are used to calculate a universal term designated as vector "a" dot vector BG mean (preferably a vector from the two daily BG means). As explained in more detail in the Example below, the eigen analysis identifies two main dimensions, the rest are noise. Therefore the vectors must be linearly related in two-dimensional (2D) space, and this drives the equations of the invention described herein. An A1C value for a patient can estimate the patient-specific offset, but the offset is not needed in order to track the AG trend, which can be performed using only the universal dot product term and typical SMBG readings. Thus, the present invention uses daily BG levels from multiple days distributed over a specified time span. According to the inter-day state-space phase portraits derived from the inter-day nonlinear dynamics of the BG levels, after one complete phase orbit 20 this universal term tracks serial AG trending (chronic glycemia trend tracking) with a precision of about less than about ±10 mg glucose per deciliter of blood (mg/dL) or less than about ±8 mg/dL, less than about ±6 mg/dL, less than about ±5 mg/dL, less than about ±4 mg/dL, or less than about ±3 mg/dL, typically about ±2.910 mg/dL. A complete orbit typically requires seven different week days (Monday, Tuesday, Wednesday, Thursday, Friday, Saturday and Sunday) over one or two adjacent weeks. The process also defines a patient-specific constant, which is the offset referred to above. This is also described in greater detail in the Example below. The 41-patient data described in the Example below covers the typical span of cases from non-insulin to insulin covering 1 to 3 months; however, there are also longer term trends such as drug adaptation/resistance, which, for greater than a 3-month time span would need another A1C value taken for the patient/subject every 3-4 months to adjust the offset value in the equations, if needed. The offset value is used to convert the relative tracking values (relative AG) to absolute AG units. The dot product using BG readings to now >~7-10 week days provide a relative AG value each day for trending. Adding a reasonable offset for each subject gives a reasonable absolute value (again, this is not necessary for trending).

Eigenanalysis of the inter-day state space of daily mean BG metrics identifies two dimensions of deterministic order and structure. The remaining dimensions represent noise fluctuations. Hence, two dimensional phase portraits can show properties of the inter-day deterministic attractor basins.

FIG. 1 illustrates a typical phase orbit 20 of daily BG mean values. The ordered flow patterns of the orbit plotted are characteristic of the deterministic dimensions. The phase orbit of daily BG readings has similar flow patterns. The two inter-day flow patterns (orbits) (as in FIG. 2) are synchronized by the two-dimensional deterministic constraint.

Figure 2:
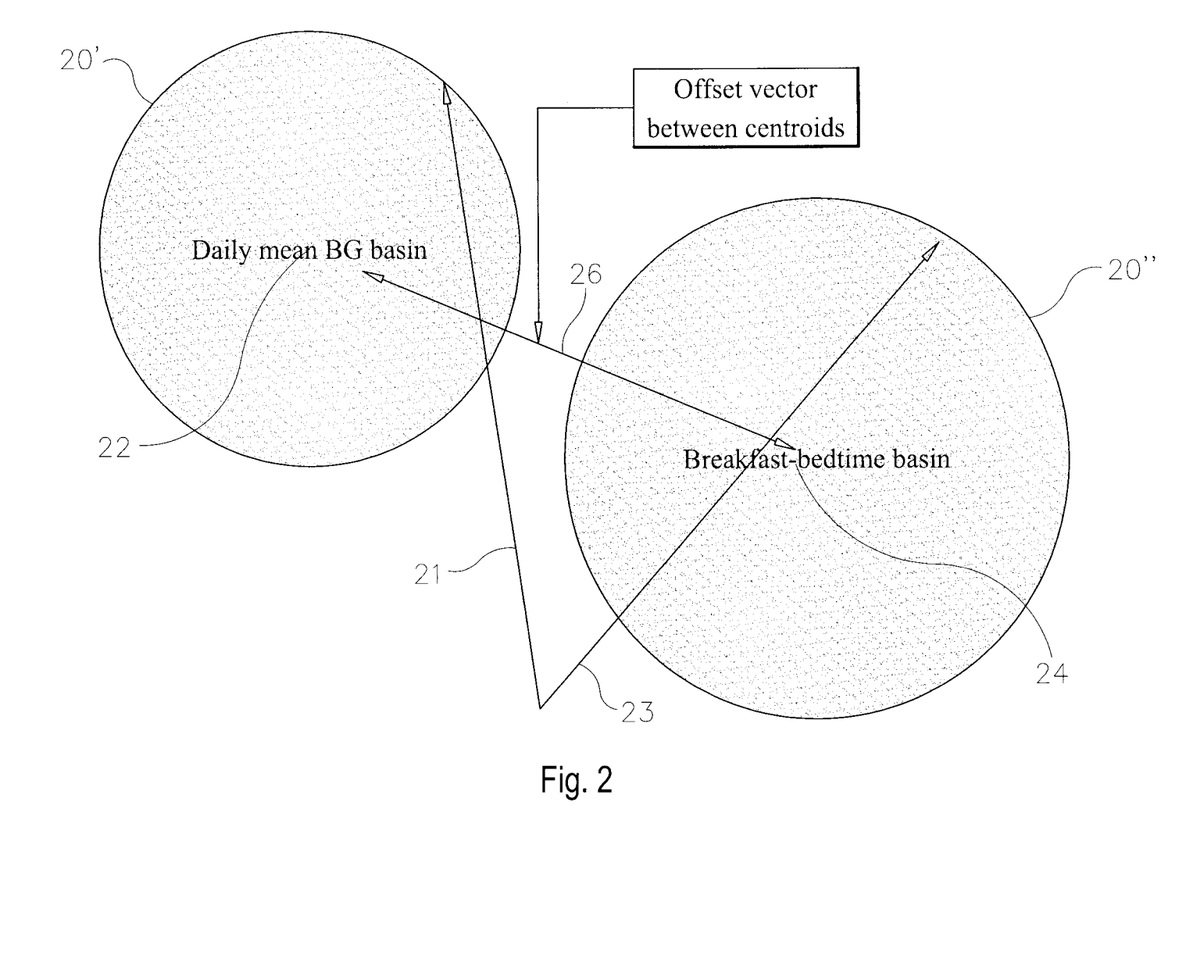
FIG. 2 shows a schematic representation of two orbits surrounding the attractor basins for daily mean BG and for paired readings vector for breakfast and bedtime BG measurements, respectively, according to an embodiment of the present invention.

FIG. 2 shows a schematic representation of two orbits 20' and 20" surrounding the attractor basins for daily mean BG and for paired readings vector for breakfast and bedtime BG measurements, respectively. One exemplary daily mean vector 21 and one exemplary daily paired readings vector 23 are shown for illustrative purposes. Of course, each orbit 20', 20" is defined by multiple vectors, as described above. The diameter of orbit 20" is larger than the diameter of orbit 20'. The daily readings are more volatile versus the daily mean although they both contain the same AG information in phase. Hence, the sum of vector "a" values is approximate to but less than one from the least squares fit. Hence, both phase portraits (i.e., orbits) show the same circular attractor basin shape/geometry in the inter-day state space of daily metrics. The diameter of the readings orbit is straightforward to determine in the representations of FIG. 2; in FIG. 1, the diameter is calculated by averaging centered vector lengths over adjacent orbits in a non-drift zone. On a month to month basis, in some patients the AG is trending (i.e., significantly changing) due to treatment (which the present invention can detect) Within each month, however, the change is small so stationarity can be approximated to consider the centered vector lengths as sufficiently stable to define non-drift zones for use in calculating the diameter of the orbit. Changes in calculated diameters over time reflect the degree of BG fluctuations (scatter), as the diameter of the readings orbit (orbit resulting from BG pair readings) is due to readings volatility. Averaging the vectors that track each circular orbit estimates the center or centroid of each attractor basin. It is noted that the average of all of the daily mean (average) blood glucose levels is by definition an evaluation of AG. That is, AG is estimated by average continuous BG readings over multiple days. The two centroids 22 and 24 are separated by an offset vector 26. Therefore, projected to the plane of the two deterministic dimensions, this centroid relation becomes $$AG_S = \text{offset}_S + a*BG \text{ mean} \pm \text{expected error} \quad [1]$$

where $AG_S$ designates the calculated chronic glycemia value or overall average blood sugar; offset, refers to a patient-specific constant that is determined by A1C value, or other methods described in more detail in the Example below; "a" is a universal constant ("a" is a vector, but here, it is assumed that the early morning bedtime readings are equivalent hence a[1]=a[2], and the value of "a" is optimized by least squares fitting to a large data set of multiple patient data; and "BG mean" is the sum of the total number of (typically two per day, but not limited to this) daily average (mean)BG readings averaged over the n ("n" being a positive integer) monitored days of a specified time interval. S indexes each subject, and the expected error is composed of both statistical uncertainty and the dynamic uncertainty of chaos theory. "Expected error" is determined by statistical analysis of a large population of patient data, as described in greater detail in the Example below.

More generally the algorithm can incorporate a parameter for each event j, where an "event" refers to any SMBG reading taken at any time:

$$AG_S = \text{offset}_S + \Sigma_j a_j * BGavg_j \pm \text{expected error}, \ 0 < a_j <= 0.5 \quad [2]$$

where "$BGavg_j$" is the daily average (mean)BG readings of event j averaged over the n monitored days of a specified time interval. However, we found the two key daily events to be sufficient, more efficient, and simpler.

In general, approximately seven initial monitored days of paired BG readings are required, at a minimum by the averaging process to adequately populate the attractor geometry and hence initiate centroid convergence of the universal term and reduce statistical and chaotic error to an acceptable level. Subject to this requirement, the formula parameters are optimized by least-squares to fit a population of patient data provided by the International Diabetes Center, IDC. The best two BG levels were at the SMBG events "before breakfast" and "bedtime".

Consequently, the optimized general formula becomes:

$$AG_S = \text{offset}_S + 0.475 * BG \text{ mean} \pm 2.910 \text{ mg/dL} \quad [3]$$

Or, expanded, with more specific definition $AG_S = \text{offset}_S + $ [0.475, 0.475] "dot" [breakfast mean BG, bedtime mean BG]' which using BG mean=breakfast mean BG+bedtime mean BG becomes upon adding the expected error.

Figure 3:
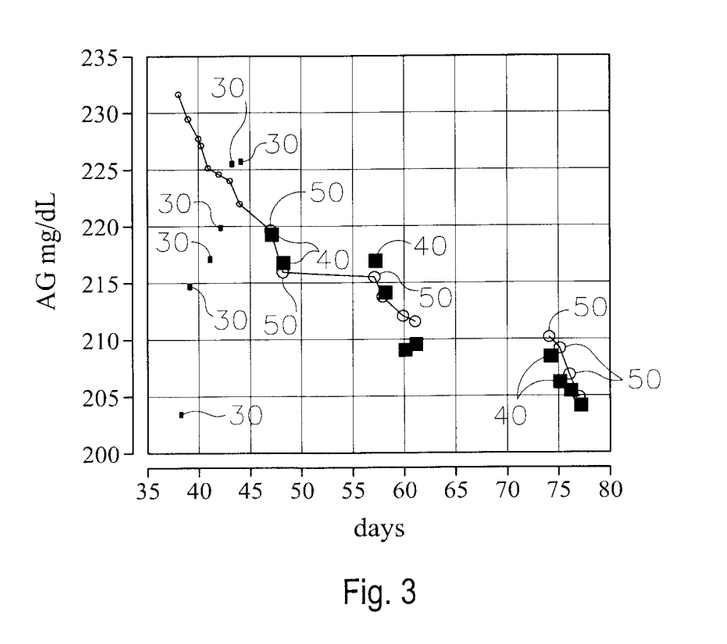
FIG. 3 shows plots of data illustrating use of the present invention as a tracking tool for chronic glycemia, according to an embodiment of the present invention.

FIG. 3 illustrates how the invention is applied as a clinical diagnostic tool. FIG. 3 shows the tracking ability of the formula [3] applied as a clinical tool. The observations for this subject are typical of clinical conditions with multiple missing monitored days covering an arbitrary span of time. Despite this, the orbital dynamics ensure consistent clinical tracking for AG. Fortunately, we can compare these clinical predictions with the IDC evaluations for AG. After the initial seven pairs of data 30 (small symbols on left) required by orbital dynamics, the formula predictions 40 calculated by use of the formula [3] applied to the data 30 in a manner described above, converge to within 3 mg/dL units of the AG values 50 (all large symbols). By tracking the plot over time, it can also be observed that there is consistent significant AG improvement of this subject who is taking an effective diabetes medication.

Similar analysis on 41 diabetes patients detected similar improvement in 16 of the 41 subjects. Statistical analysis of the inter-day BG orbits also detected four subjects having significant changes in radius (BG scatter) over the time span of their data. Two subjects became worse (increased scatter) and two got better. This is discussed in greater detail in the Example below.

Figure 4:
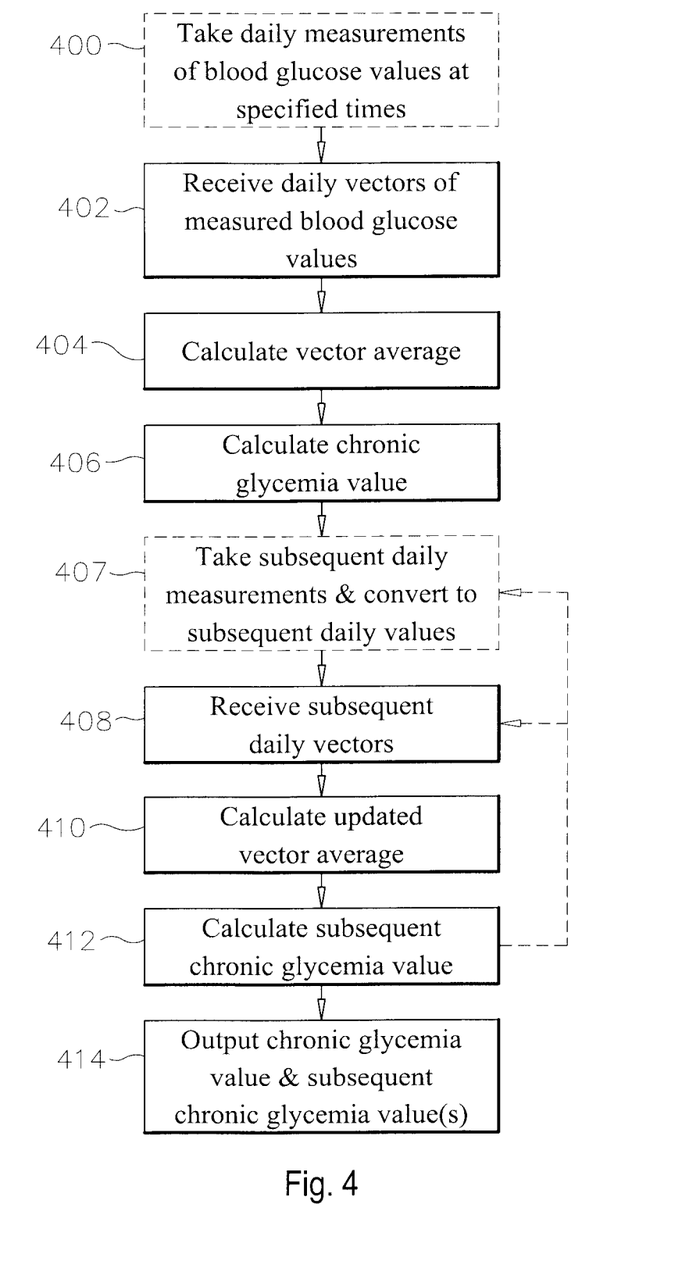
FIG. 4 shows events that may carried out for tracking chronic glycemia according to an embodiment of the present invention.

FIG. 4 shows events that may be carried out for tracking chronic glycemia according to an embodiment of the present invention. Processing of events are carried out by one or more processors of an apparatus according to an embodiment of the present invention, one or more or all of which may be incorporated into a handheld personal blood glucose monitoring device, such a the ONE TOUCH ULTRA 2 Blood Glucose Monitor (Lifescan, Inc, Milpitas, Calif.) or any other commercially available blood glucose monitor. Additionally or alternatively, some or all events can be carried out by one or more processors located externally of a blood glucose monitoring device, using blood glucose readings taken from the blood glucose monitoring device or from multiple glucose monitoring devices. Still further alternatively, these events can be performed by non-portable apparatus including blood monitoring capability, such as apparatus in a hospital, lab or doctor's office. At event 402, daily vectors of measured blood glucose level values ordered by daily-defined time points over multiple days distributed over a predefined time period are received. These daily vectors may be imported by the apparatus, as received wirelessly (or by wired network or telephone connection) from a blood glucose monitor, or by inputting the vector data by any other known conventional method of inputting data. Alternatively, when incorporated into a blood glucose monitoring device, daily measurements of blood glucose values are taken at the specified times and the daily vectors are calculated from these measurements and then provided at event 402.

At event 404, a vector average is calculated from the daily vectors. At event 406, a chronic glycemia value is calculated based on the vector average modified by a universal term based on the centroid of an attractor basin estimated by an orbit established by the daily vectors calculated from the blood glucose levels measured at the defined time points over multiple days distributed over the predefined time period, such as by processing using the formula [3].

At event 408, subsequent daily vectors of blood glucose level values measured at subsequent defined time points after the predefined time period are received. Similar to event 400, optionally, at event 407, when an integrate monitoring device is use, the blood glucose level values may be taken by the device and subsequent daily vectors are calculated to provide the input for event 408, or the subsequent daily vectors can be received by any of the other methods described above. At event 410, an updated vector average is calculated from the daily vectors and subsequent daily vectors. At event 412 a subsequent chronic glycemia value based on the updated vector average modified by the universal term based on the centroid of the attractor basin estimated from the orbit, such as by processing using the formula [3]. The events 408-412 (and optionally, 407) can be iterated as many times as desired to generate chronic glycemic values over an extended time period, with each iteration providing an additional subsequent chronic glycemia value. At event 414, the chronic glycemia value and subsequent chronic glycemia value(s) are outputted. The output can take the form of displaying the values, printing out the values, transmitting the values to another computer device, plotting the values, either on paper or a display, transmitting a plot, or any other known means of outputting. Outputting may also include storing the values and/or lots in a storage medium.

Figure 5:
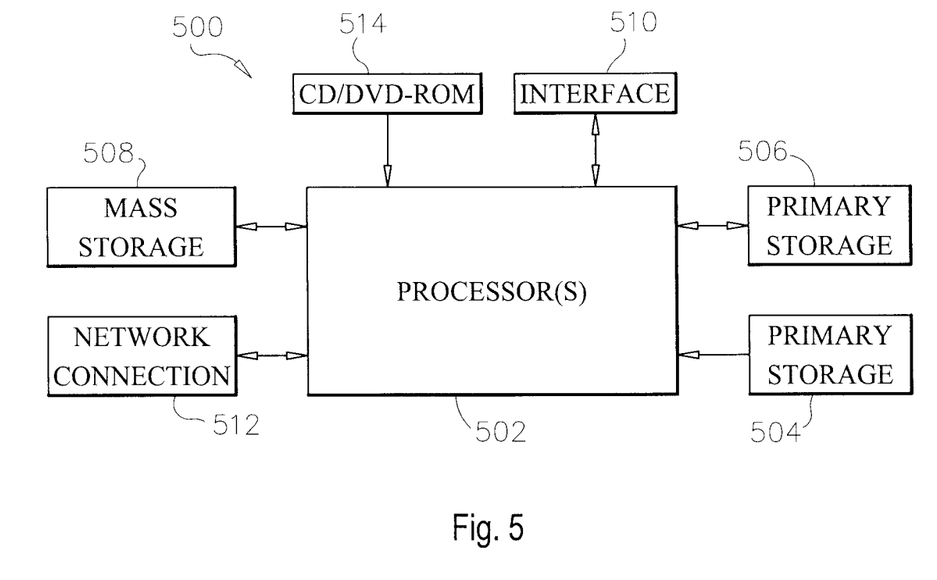
FIG. 5 is a block diagram of a computer system that may be implemented as an apparatus for performing events according to an embodiment of the present invention.

FIG. 5 is a block diagram of a computer system that may be implemented as an apparatus for performing events such as those described with regard to FIG. 4 and elsewhere throughout the specification, according to an embodiment of the present invention. Some or all of these components may be incorporated into a blood glucose monitor, as described previously. Alternatively, some or all of thee component may be provided in an apparatus that is separate from a blood glucose monitor, with the apparatus being configured to receive blood glucose measurement date and/or vectors. This figure represents a typical computer system, components of which, or all of which may be employed in an apparatus according to an embodiment of the present invention. The computer system 500 includes any number of processors 502 (also referred to as central processing units, or CPUs, and, for example, which may be employed in a blood glucose monitor or other apparatus) that are coupled to storage devices including primary storage 506 (typically a random access memory, or RAM), primary storage 504 (typically a read only memory, or ROM). As is well known in the art, primary storage 504 acts to transfer data and instructions uni-directionally to the CPU and primary storage 506 is used typically to transfer data and instructions in a bi-directional manner. Both of these primary storage devices may include any suitable computer-readable media such as those described above, but will typically be solid state memory/devices. A mass storage device 508 may also be coupled bi-directionally to CPU 502 to provide additional data storage capacity and may include any of the computer-readable media described above. When incorporated into a blood glucose monitoring device, mass storage device 508 will typically be solid state memory, either using the memory already existing in the blood glucose monitoring device, or additional solid state memory. Mass storage device 508 may be used to store programs, data and the like. It will be appreciated that the information retained within the mass storage device 508, may, in appropriate cases, be incorporated in standard fashion as part of primary storage 506 as virtual memory. A specific mass storage device such as a CD-ROM or DVD-ROM 514 may optionally also pass data uni-directionally to the CPU.

CPU 502 is also coupled to an interface 510 that includes one or more input/output devices such as buttons, video monitors, track balls, mice, keyboards, microphones, touch-sensitive displays, transducer card readers, magnetic or paper tape readers, tablets, styluses, voice or handwriting recognizers, or other well-known input devices such as, of course, other computers. Interface 510 may include interfaces to other computers, an interface to the blood glucose monitor, and the like. CPU 502 optionally may be coupled to a computer or telecommunications network using a network connection as shown generally at 512, which may be a wired interface, or wireless, such as a WiFi interface or BLUETOOTH interface or the like. With such a network connection, it is contemplated that the CPU might receive information from the network, or might output information to the network in the course of performing the above-described events. The above-described devices and materials will be familiar to those of skill in the computer hardware and software arts.

It is further intended that any other embodiments of the present invention that result from any changes in application or method of use or operation, method of manufacture, shape, size, or material which are not specified within the detailed written description or illustrations contained herein yet are considered apparent or obvious to one skilled in the art are within the scope of the present invention.

EXAMPLE

In order to test the clinical applications of the present invention and validate the diagnostic formula [3] for AG, the International Diabetes Center (IDC) provided 1-4 months of continuous glucose monitoring (CGM) data for forty-one male and female subjects at sampling rates of 5 or 10 minutes. Personal and patient-specific information were not provided. All subjects took prescription medications for Type 2 diabetes, and thirty required insulin. The sampling rates of the continuous BG readings provided an inter-day daily BG mean not possible with the sparse individual events of SMBG readings that the present invention is adapted for. In addition, CGM profiles also capture such individual events, vis, BG levels before and after meals and at bedtime. Some days were missing and other removed for excessively missing readings (those having greater than 15% missing readings). Days were also excluded if key SMBG events were not identified in the profiles. Consequently, there were 940 evaluable CGM subject days out of a possible 1734 CGM subject days.

Standard statistical methods were used to remove subject-to-subject (inter-subject) variations from all data. Then, using the simple single(singular)-variable embedding method of nonlinear dynamics (e.g., see Holt T A, Editor. "Complexity for Clinicians". Radcliffe, 2004 and Kroll MH, "Biological variation of glucose and insulin includes a deterministic chaotic component", Biosystems, 50:89-210, 1999, both of which are hereby incorporated herein, in their entireties, by reference thereto) an inter-day state space matrix was formed from the vector to time-ordered evaluations of the inter-day daily blood glucose mean values for all subjects. The inter-day daily BG levels at specific SMBG-defined events were each added as a separate column to this matrix.

In general, singular-value decomposition of a data matrix produces geometric information about the pattern of data points in the coordinate space of the matrix columns used as variables. Singular-value analysis of the state-space matrix in this example revealed that the inter-day time-ordered variations were composed of many dimensions of noise and only two dimensions of structure and order, as characterized by deterministic chaos. This implies that the state-space data pattern (or "orbit", as referred to above) obeys the attractor geometry of a two-dimensional fuzzy disk. Consequently, it was determined that there is a linear relation among more than two independent deterministic columns of the inter-day BG data. From this constraint (i.e., the linear relationship) a universal relationship applicable to all subjects was created for the inter-day daily mean in terms of two daily BG levels plus noise. Returning the inter-subject variations back into this intra-subject columns caused the universal equation to acquire a subject-specific offset (i.e., a constant, see $offset_S$ in equation [3] above) in addition to the universal function of the two BG levels. Also, the AG and BG columns regained the multiday gradient progression specific to the diabetes of each subject.

For clinical application, the two best BG levels were found to be: (1) the beginning of the day (early morning, pre-breakfast) and (2) the end of the day (before bedtime). Fortuitously, these two best BG levels are also typical SMBG events. They tend to capture two expected distinct, basic levels of daily liver activity associated with active modes versus rest/sleep mode of daily metabolic processes. The formula for AG (e.g., see formula [3] above) was created by replacing all inter-day variables in the equation by their average over a specified multiple of days. This estimates the geometric enters of their attractor basins, making the equation a formula relating the attractor two basin centroids (e.g., see FIG. 2). The final result was a formula for AG in terms of the average of individual BG levels. For each monitored ay of the forty-one subjects, the before-breakfast and bedtime BG levels were inserted into the inter-day equation along with the daily mean level. To predict chronic glycemia, the equation and its variables are averaged over a set of monitored days chronologically distributed over a specific time interval of interest. The set of days must also generate one or more complete weekday phase cycles to adequately populate the inter-day attractor's geometry. The offset parameter (i.e., see $offset_S$ in equations [1]-[3] above) for each subject and the universal parameter (i.e., "a" in equation [1] above) were determined using the population leverage of the IDC data. Hence, by this method all formal parameters were optimized by a least-squares fit of all progressive time intervals of AG evaluations for all forty-one subjects. To evaluate the robustness of the method, each subject in turn was excluded from the data and the parameters were re-optimized. A measure of robustness was calculated as the standard deviation, using the forty-one parameter estimates.

To test the clinical utility, the optimized formula (formula [3] above) was applied to predict AG for both early (after the first ten days) and full-term (CGM endpoints) of each subject and also to detect and track AG time trends for one selected patient under clinical conditions. All statistical data analysis for this example and (for the detailed description above) was performed using JMP® 8.02 of SAS Institute, Inc., Cary, N.C.

Figure 6:
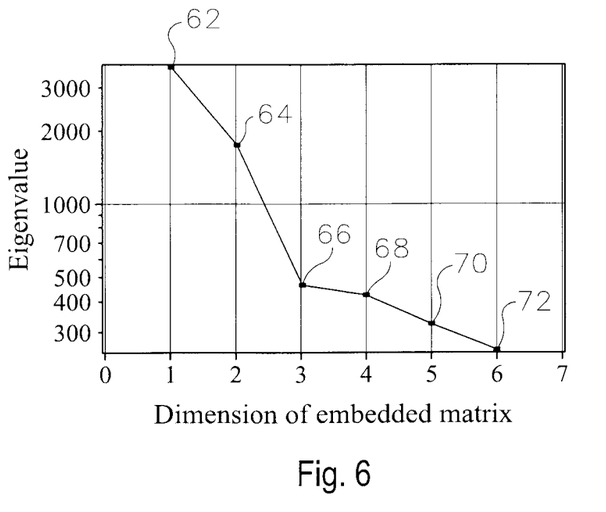
FIG. 6 shows results of a singular value analysis, also referred to an eigenanalysis, of an intra-subject, inter-day, state-space matrix provided in an Example according to an embodiment of the present invention.

FIG. 6 shows the singular value analysis, also referred to an eigenanalysis, of the intra-subject, inter-day, state-space matrix showing that two initial prominent dimensions (62 and 64, respectively) account for 79% of the serial inter-day variations, while the other 21% are noise dimensions (66, 68, 70 and 72). FIG. 6 depicts this drop to the noise levels after the first two deterministic dimensions (62 and 64) representing ordered and structured inter-day patterns. Hence, any two independent state-space variables can produce the state-space phase portraits reflecting the disk-like attractor basins of the inter-day glycemic dynamics.

FIG. 1 displays a ten-day sample from the orbit pattern of the daily BG mean values centered on their attractor centroid for one subject. The orbit appears to have circular, quasi-weekly cycles where the first eight days indicate a complete orbital rotation from Saturday to Saturday, where the Saturdays are referenced by numerals 1 and 8, respectively. Hence, the discrete series of inter-day BG mean values over the days of a specific time span appears to originate from a deterministic chaotic process producing elliptical phase patterns within a two-dimensional attractor basin (disk) whose geometric center by definition is AG.

As expected, averaging of the inter-day daily mean values over n (positive integer representing the number of monitored days of samples) monitored days estimated the attractor's centroid, which is the value for chronic glycemia monitoring (i.e., AG). Simultaneously averaging the inter-day pairs of key BG levels estimates the attractor centroid for this data. As described previously, this simultaneous average process created the following formula for the AG of each subject (S):

$$AG_S = \text{offset}_S + a \, {}^*BG \text{ mean} \pm \text{expected error} \quad [1]$$

wherein "BG mean" is the average of the sum of the two key daily BG readings (i.e., before breakfast and just prior to bedtime) for the n monitored days of a specified time span. "S" indexes each subject, and the expected error is composed of both statistical uncertainty and the dynamic uncertainty of chaos theory. The values of all parameters, i.e., the universal "a", the forty-one personal "offset$_{(S)}$" values and "expected error" were determined using the population of all IDC data. In general, as suggested by FIG. 1, at least approximately seven monitored individual weekdays of paired BG readings are required by the averaging process to adequately populate the attractor geometry and hence initiate convergence toward the basin centroid while also reducing statistical and chaotic error to an acceptable level. To minimize the impact of potential inter-day gradients, these weekday should be distributed within a span of two or three weeks. Subject to this requirement, the formula parameters were optimized by least-squares to fit the IDC data.

Consequently, the optimized general formula predicting all 653 converged AG evaluations became:

$$AG_S = \text{offset}_S + 0.475 \, {}^*BG \text{ mean} \pm 2.910 \text{ mg/dL} \quad [3]$$

The robustness standard derivation for the universal parameter 0.475 evaluated to be ±0.0007, indicating very good independence from subject selection. From statistical theory the precision error (±2.910 md/dL) was unexpected, when using a conventional method, since a conventional least-squares model predicting the daily BG mean values of each subject by these to-paired BG levels produced a median error of ±17 mg/dL for this subject population.

Figure 7:
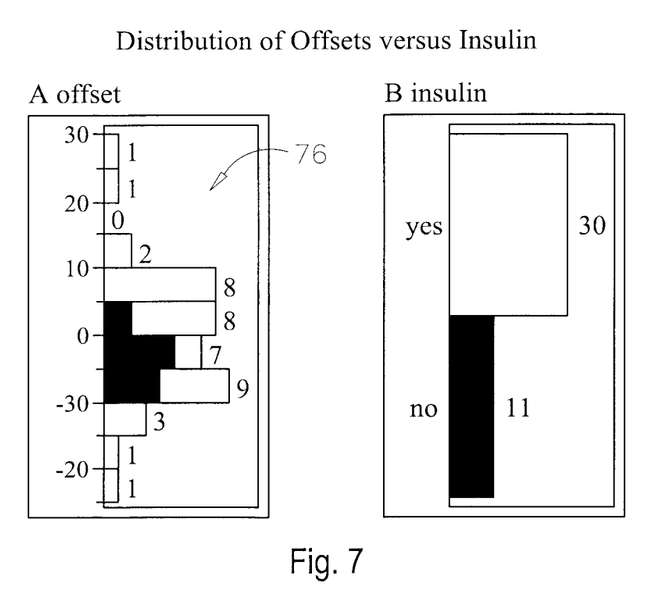
FIG. 7 shows a histogram of forty-one offset values individually applied to forty-one patients in an Example performed according to an embodiment of the present invention.

Offset level is a measure of the persistence of BG event excursions relative to the two key BG levels in the formula. This persistence is impacted by insulin resistance and relates to disease progression. The histogram 76 of the forty-one offset values individually applied to the forty-one patients in the example, respectively, is shown in FIG. 7, with the insulin count (indicating advanced diabetes) unshaded, with the rest of the population shaded. The offset values are centered about zero, while insulin users extend to more extreme levels. The tracking precision of the universal term "a" in the formula is independent of the offset value. Subject-offset estimates were obtained from the CGM data in this example, but can also be obtained using A1C tables, or using cluster-correction methods that have been found to be effective in other diagnostic applications (e.g., see Martinet-Peignouz et al., "Accurate model predicting sustained response at week 4 of therapy with pegylated interferon with ribavirin in patients with chronic hepatitis C", Journal of viral Hepatitis, 13(10): 701-707, 2006; Minor, "Similarity least Square (SLS) method for Functional Clustering by Using Stimulus Features to Model and Predict response", dlsguy.com, 2004; and Rickey et al, "Predictors of Improvement in lower Urinary Tract Symptoms after Sacrocolpopexy", Society for Urodynamics and Female Urology, Phoenix, AX (oral presentation), February, 2011, each of which is hereby incorporated herein, in its entirety, by reference thereto). Hence, for any patient, the term "0.475*BG mean" can be applied to monitor AG changes on a daily basis with great precision. The personal offset level determines the absolute value of AG that is typically compared to clinical thresholds in medical references, but is not required for relative AG tracking. Accordingly, for relative AG tracking the formula used can generally be:

$$\text{relative} AG_S = a_S \, {}^*BG \text{ mean} \pm \text{expected error} \quad [4]$$

Or, specifically:

$$\text{relative} AG_S = 0.475 \, {}^*BG \text{ mean} \pm 2.910 \text{ mg/dL} \quad [5]$$

FIG. 3 shows that tracking ability of the present invention as a clinical tool. The observations for the subject represented in FIG. 3 are typical of clinical conditions with multiple missing monitored days covering an arbitrary span of time. Despite this, the inter-day orbital dynamics ensured consistent clinical tracking for AG. These clinical predictions were compared with the CGM evaluations for AG. As expected from the orbital patterns, after the initial seven pairs of weekday data (indicated by reference numeral 30), the formula predictions 40 converged to within 3 mg/dL units of the AG values 50. Consistent significant improvement of the AG values of the subject over time can be observed, confirming that the subject was taking an effective diabetes medication.

Statistical analysis of all subjects detected only four subjects having significant changes in radius (BG scatter) over the terms of the IDC data. Two of the subjects became worse (increased scatter) and two got better.

In summary, after seven initial pairs of weekday BG readings within two weeks as described: (1) the present invention evaluated chronic glycemia for all subjects on a daily basis with an error standard deviation of ±2.91 mg/dL; (2) the error standard deviation specific to the last day (full term) Ag was ±2.54 mg/dL; and (3) the error standard deviation of AG using the initial ten paired BG readings was ±3.05 mg/dL. Whereas the IDC data indicates slow AG trends over multiple weeks, the personal offset value depends on intrinsic disease properties with trends over many months.

The inter-day daily mean values of continuous BG levels exhibited the properties of discrete serial data of a deterministic chaotic process. Consequently, daily BG levels of two paired SMBG events were found to approximate the CGM inter-day daily means as they evolve over time of several months JMM. Based on this synchronization, the present invention tracks AG trends on a daily basis with unprecedented precision. Independently of precision, accuracy for AG level is determined by an offset constant for each subject. In practice, this offset constant is determined by CGM data or HbA1C measurements. Thus, the present invention provides the following clinical tools for diabetes: (1) tracking trends of chronic glycemia with an improved precision error over what has been known; (2) evaluation of chronic glycemia on a daily basis; (3) detection of a significant change in chronic glycemia within two weeks after an intervention; (4) measurement of BG scatter and the trending of the same over time; and (5) evaluation of the quality of BG readings by inter-day phase plots and attractor properties.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A computer apparatus for performing at least one of diagnosing or monitoring chronic glycemia, said apparatus comprising:
at least one processor; and
programming which, when executed by said at least one processor, performs a process including:
receiving daily vectors of measured blood glucose level values ordered by daily-defined time points over multiple days distributed over a predefined time period;
calculating a vector average from the daily vectors;
calculating a chronic glycemia value based on the vector average modified by a universal term based on the centroid of an attractor basin estimated by an orbit established by the daily vectors calculated from the blood glucose levels measured at the defined time points over multiple days distributed over the predefined time period;
receiving subsequent daily vectors of blood glucose level values measured at subsequent defined time points after the predefined time period;
calculating an updated vector average from the daily vectors and subsequent daily vectors;
calculating a subsequent chronic glycemia value based on the updated vector average modified by the universal term based on the centroid of the attractor basin estimated from the orbit; and
outputting the chronic glycemia value and subsequent chronic glycemia value to show a trend over time of chronic glycemia status.

2. The computer apparatus of claim 1, wherein said programming, when executed by said at least one processor, outputs the chronic glycemia value after said calculating a chronic glycemia value.

3. The computer apparatus of claim 1, wherein said calculating a chronic glycemia value comprises calculating the chronic glycemia value using the formula:

$$AG_S = \text{offset}_S + \text{vector } a * \text{vector } BG \text{ mean} \pm \text{expected error};$$

where "$AG_S$" refers to the chronic glycemia value, * indicates a vector dot product operation, $\text{offset}_S$ is a patient-specific constant, "vector a" is a vector that refers to said universal term," vector BG mean" is a vector that refers to said vector average, "S" indexes each subject, and said expected error results from both statistical uncertainty and dynamic uncertainty of chaos theory.

4. The computer apparatus of claim 3, wherein said vector "a" is a two-dimensional vector comprising components "a[1]" and "a[2]", and wherein $0 < a[1] < 0.5$ and $0 < a[2] \leq 0.5$.

5. The computer apparatus of claim 3, wherein said vector "a" is a two-dimensional vector comprising components "a[1]" and "a[2]", and wherein $0 < a[1] \leq 1.0$ and $0 < a[2] \leq 1.0$.

6. The computer apparatus of claim 3, wherein $a[1] = a[2] = 0.475$, and expected error $= \pm 2.910$ mg/dL.

7. The computer apparatus of claim 3, wherein said expected error is less than $\pm 10$ mg/dL (glucose/blood).

8. The computer apparatus of claim 3, wherein said expected error is about $\pm 2.91$ mg/dL (glucose/blood).

9. The computer apparatus of claim 1, wherein said calculating a chronic glycemia value comprises calculating a relative chronic glycemia value using the formula:
AGs =vector a* vector BG mean ±expected error;
where "$AG_S$" refers to the chronic glycemia value, * is a vector dot product, "vector a" is a vector that refers to said universal term, "vector BG mean" is a vector that refers to said vector average, "S" indexes each subject, and said expected error results from both statistical uncertainty and dynamic uncertainty of chaos theory.

10. The computer apparatus of claim 1 incorporated in a personal blood glucose monitor.

11. The computer apparatus of claim 1, wherein said programming, when executed by said at least one processor, calculates at least one scatter value based on a diameter of said orbit, and outputs said at least one scatter value, wherein each said at least one scatter value is calculated by averaging diameter values of said orbit over multiple adjacent time periods.

12. A chronic glycemia monitoring apparatus comprising:
a blood glucose monitoring device configured to take and output blood glucose measurements, including at least one processor;
said apparatus further comprising programming which, when executed by said at least one processor, performs a process including:
receiving daily blood glucose level values measured by said blood glucose monitoring device at daily-defined time points over multiple days distributed over a predefined time period;
calculating a daily vector of the measured blood glucose level values received for each day, respectively;
calculating a vector average from the daily vectors having been calculated;
calculating a chronic glycemia value based on the vector average modified by a universal term based on a centroid of an attractor basin defined by a vector orbit established by the blood glucose levels measured at the defined time points over multiple days distributed over the predefined time period;
receiving subsequent blood glucose level values measured by said blood glucose monitoring device on one or more days after the predefined time period;
calculating a subsequent daily vector of measured additional blood glucose level values received for each day, respectively, after the predefined time period;
calculating an updated vector average from the daily vectors and subsequent daily vectors;
calculating a subsequent chronic glycemia value based on the updated vector average modified by the universal term based on the centroid of the attractor basin estimated from the vector orbit; and
outputting the chronic glycemia value and subsequent chronic glycemia value to show a trend over time of chronic glycemia status.

13. A non-transitory computer readable medium including one or more sequences of instructions for performing chronic glycemia trending, wherein execution of the one or more sequences of instructions by one or more processors causes the one or more processors to perform a process comprising:
receiving a daily vector of measured blood glucose level values ordered by daily defined time points over multiple days distributed over a predefined time period;
calculating a vector average from the daily vectors of blood glucose levels received;
calculating a chronic glycemia value based on the vector average modified by a universal term based on a centroid of an attractor basin estimated by an orbit established by the daily vectors of the blood glucose levels measured at the defined time points over multiple days distributed over the predefined time period;

receiving at least one additional daily vector of blood glucose level values measured at additional defined time points after the predefined time period;

calculating an updated average vector blood glucose level from the daily vectors and said at least one additional daily vector;

calculating a subsequent chronic glycemia value based on the updated vector average modified by the universal term based on the centroid of the attractor basin estimated from the orbit; and outputting the chronic glycemia value and subsequent chronic glycemia value to show a trend over time of chronic glycemia status.

14. The non-transitory computer readable medium of claim 13, further including instructions which, when executed by the one or more processors, cause the one or more processors to output the chronic glycemia value after said calculating a chronic glycemia value.

15. The non-transitory computer readable medium of claim 13, wherein said calculating a chronic glycemia value comprises calculating the chronic glycemia value using the formula:

$$AG_S = \text{offset}_S + a * BG \text{ mean} \pm \text{expected error};$$

where "$AG_S$" refers to the chronic glycemia value, * indicates a vector dot product operation, $\text{offset}_S$ is a patient-specific constant "a" is a vector that refers to said universal term, "BG mean" is a vector that refers to said vector average, "S" indexes each subject, and said expected error results from both statistical uncertainty and dynamic uncertainty of chaos theory.

16. The non-transitory computer readable medium of claim 15, wherein said vector "a" is a two-dimensional vector comprising components "a[1]" and "a[2]", and wherein $0 < a[1] \leq 0.5$ and $0 < a[2] \leq 0.5$.

17. The non-transitory computer readable medium of claim 15, wherein said expected error is less than ±8 mg/dL (glucose/blood).

18. The non-transitory computer readable medium of claim 15, wherein said expected error is about ±2.910 mg/dL (glucose/blood).

19. The non-transitory computer readable medium of claim 13, further including instructions which, when executed by the one or more processors, cause the one or more processors to calculate at least one scatter value based on a diameter variation of said orbit over time, and output said at least one scatter value.

20. A method for tracking chronic glycemia, said method comprising:

receiving a daily vector of measured blood glucose level values ordered by daily defined time points over multiple days distributed over a predefined time period;

calculating a vector average from the blood glucose levels received over multiple days;

calculating a chronic glycemia value based on the vector average modified by a universal term based on a centroid of an attractor basin estimated by an orbit established by the vectors of the blood glucose levels measured at the defined time points over multiple days distributed over the predefined time period;

receiving at least one additional daily vector of blood glucose level values measured at additional defined time points after the predefined time period;

calculating an updated vector average from the blood glucose levels and the additional blood glucose levels received;

calculating a subsequent chronic glycemia value based on the updated vector average modified by the universal term based on the centroid of the attractor basin estimated by the orbit; and outputting the chronic glycemia value and subsequent chronic glycemia value to show a trend over time of chronic glycemia status.

21. The method of claim 20, wherein said calculating a chronic glycemia value comprises calculating the chronic glycemia value using the formula:

$$AG_S = \text{offset}_S + \text{vector } a * \text{vector } BG \text{ mean} \pm \text{expected error};$$

where "$AG_S$" refers to the chronic glycemia value, * indicates a vector dot product operation, $\text{offset}_S$ is a patient-specific constant "vector a" is a vector that refers to said universal term, "vector BG mean" is a vector that refers to said vector average, "S" indexes each subject, and said expected error results from both statistical uncertainty and dynamic uncertainty of chaos theory.

22. The method of claim 21, wherein said expected error is less than ±10 mg/dL (glucose/blood).

23. The method of claim 20, further comprising calculating at least one scatter value based on a diameter change of said orbit.

* * * * *